United States Patent [19]

McGaughey et al.

[11] Patent Number: 4,464,177
[45] Date of Patent: Aug. 7, 1984

[54] DIFFERENTIAL PRESSURE DEVICE FOR ACCELERATED CATHETER FLASHBACK

[75] Inventors: John McGaughey, Tampa; W. Patrick McVay, Clearwater; William Lauer, Valrico, all of Fla.

[73] Assignee: Critikon, Inc., Tampa, Fla.

[21] Appl. No.: 442,388

[22] Filed: Nov. 17, 1982

[51] Int. Cl.³ .............................................. A61M 5/00
[52] U.S. Cl. ................................... 604/168; 164/900; 128/765; 251/9
[58] Field of Search ................ 604/168, 900; 128/765, 128/767; 251/4, 9

[56] References Cited

U.S. PATENT DOCUMENTS

| 3,459,183 | 8/1969 | Ring et al. | 128/767 X |
| 4,020,836 | 5/1977 | Cunningham | 604/900 X |
| 4,108,175 | 8/1978 | Orton | 604/900 X |
| 4,265,425 | 5/1981 | Morin | 251/9 |
| 4,328,834 | 5/1982 | Oates, Sr. et al. | 251/9 |
| 4,365,630 | 12/1982 | McFarlane | 604/900 X |

Primary Examiner—Stephen C. Pellegrino
Attorney, Agent, or Firm—Audley A. Ciamporcero, Jr.

[57] ABSTRACT

A pair of compressible, hinged opposing arms enclose a bladder chamber, which in turn is coupled to the catheter. As the arms are compressed together, successive pivot fulcra close, in turn first pinching and closing, and then opening the bladder to create negative differential pressure against the catheter, and promoting flashback.

5 Claims, 7 Drawing Figures

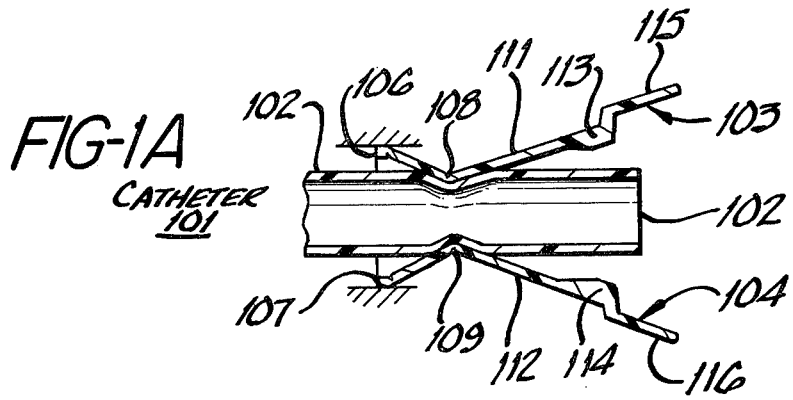
FIG-1A Catheter 101
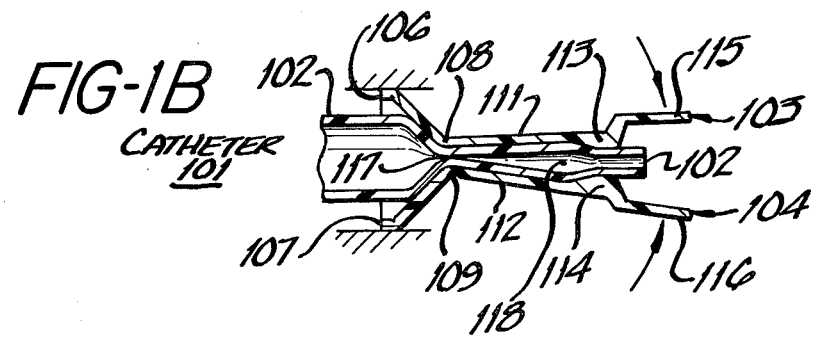
FIG-1B Catheter 101
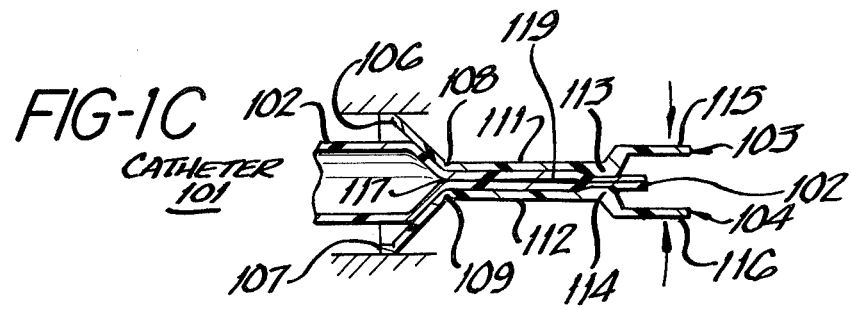
FIG-1C Catheter 101
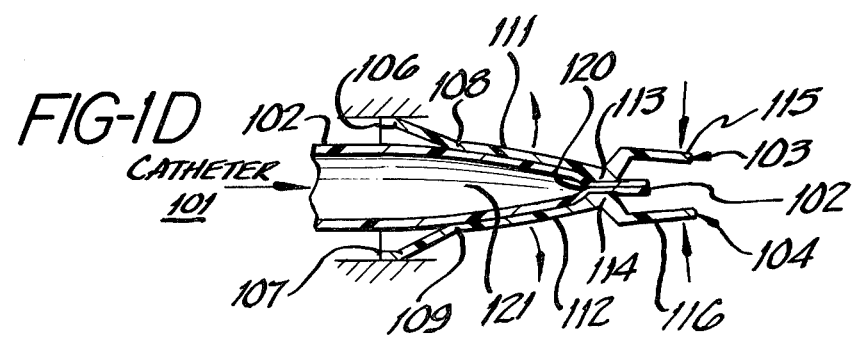
FIG-1D Catheter 101

DIFFERENTIAL PRESSURE DEVICE FOR ACCELERATED CATHETER FLASHBACK

FIELD OF THE INVENTION

This invention relates to vascular fluid administration devices, and more particularly to apparatus for accelerating blood flashback in intravenous catheters.

BACKGROUND OF THE INVENTION

Direct vascular administration of medicaments and nutritional fluids has become the preferred mode of treatment for substantially all critically ill patients, as well as for numerous patients with chronic conditions. Indwelling intravenous (and occasionally, intra-arterial) catheters have for the most part replaced rigid needles as the preferred vehicle for vascular fluid administration. Catheter markets are generally held to be expanding rapidly, indicating general acceptance through the worldwide medical community; improvements in catheter structure and operation further permit utilization for still further medical applications.

Conventionally, such catheters include an assembly in which a flexible tube, for example of polymeric construction, is bonded to a hub, and the assembly is carried about a removable cannula which extends slightly beyond the extremity of the tube. The catheter is set in place by easing the assembly into the flesh of the patient until it just penetrates the vascular wall. When the device is so set, the cannula is removed, leaving the catheter tube indwelling. Fluid administration sets, pumps, or the like are coupled to the hub, and suitable medicinal or nutritional fluids are delivered to the patient directly into the blood.

Probably the most accepted objective method for determining the proper placement of a catheter is the occurrence of "flashback", or backflow of blood up through the catheter, in some cases into a visible reservoir in the catheter hub. Of course, since the catheter insertion process is often quite swift, it is desirable that the flashback response time be very brief, thereby to give the treating physician or nurse a fast, essentially "real time" indication of the actual position of the catheter tip. Clearly, if the flashback response time is unduly slow, the flashback function will at best be of no use to the treating physician or nurse, and at worst will be totally misleading. For example, it is desirable that the flashback function occur quickly enough to avoid cannula penetration through the back wall of the vasculature and into surrounding tissue. Likewise, it is most desirable to have a flashback acceleration scheme which may be safely used in very low blood pressure situations, such as cardiac arrest or tourniquet applications.

It is a primary object of the present invention to provide apparatus for accelerating the flashback response time in intravascular catheters.

One method, to which the principles of the present invention ultimately relate, for accelerating flashback response time, is to create a slight vacuum in a flashback chamber within the catheter hub, thereby to accelerate the flow of blood back through the cannula for indication of proper placement. Often, this is done by means of a syringe, which is coupled to the catheter, and which creates a negative pressure differential as the plunger is withdrawn. Of course, in creating the partial vacuum, it is necessary to insure that air emboli or the like are not forced through the catheter and into the vascular system of the patient. It is likewise important that the partial vacuum be as slight as possible while being effective, lest vascular collapse or tissue withdrawal be accidently caused.

It is accordingly a further object of the present invention to provide a device for accelerated flashback response time safely utilizing the vacuum pull method, while avoiding the risk of unintentional deposit of fluid, air, or the like undesirable foreign substances into the blood stream.

CROSS REFERENCE TO RELATED APPLICATIONS

Reference is made to concurrently filed, copending application U.S. Ser. No. 442,389 which also relates to flashback acceleration.

SUMMARY OF THE INVENTION

In accordance with the principles of the present invention, an elastomeric bladder is either included in, or coupled to the catheter needle, and forced to create a partial vacuum through application of compressive force by opposing hingedly connected compression arms. In particular, the arms are so configured as to define a succession (e.g., a pair) of respectively successively closeable pincer fulcra. As the arms are compressed together, a first pair of oppositely opposing areas or ridges close together thereby proximally to close the flexible bladder, and further to act as a pivot fulcrum for the next portion of the compression phase. During this next portion, and until the closure of the second fulcrum, the bladder is evacuated distally over a portion of its length while the first fulcrum closure prevents such evacuation from communicating with the catheter. After the second fulcrum is closed, further compression of the arms causes the first fulcrum to open, and the proximal segment of the bladder to reopen as well, communicating with the catheter and drawing a slight vacuum therefrom. As the catheter tip is properly placed, the vacuum will enhance the flashback function, even in very small gauge catheters.

In a preferred embodiment, the bladder and compression arm assembly is attached to a convention catheter needle hub integrally or through a luer connection. The bladder is vented on the opposite or distal side. Advantageously, the bladder evacuation process, with creation of the consequent partial vacuum, occurs when the catheter needle is subcutaneous, but before or at the time in which the needle has penetrated the vein. As the needle penetrates the vein, the blood instantaneously flows back into the chamber because of the reduced pressure therein. Such a unit is especially valuable for use in small gauge catheters, or in cases wherein the patient has low blood pressure or is in shock, in which case the normal unassisted flashback function would be retarded because of a deficiency in vascular pressure.

It is a feature of the present invention that a partial vacuum of safe magnitude is set up without substantial danger of introduction of air emboli into the vascular system. In particular, the first fulcrum closure tends to isolate the catheter and the patient from the evacuation process, and once this is completed, the second fulcrum creates the proximal pull on the flashback chamber.

It is another significant feature that embodiments of the present invention may be safely used to advantage in numerous fluid aspiration and sampling procedures.

DESCRIPTION OF THE DRAWINGS

FIGS. 1A through 1D show in schematic fashion a preferred embodiment of the principles of the present invention, and its operation in successive views for creation of a flashback enhancing partial vacuum.

BEST MODE FOR CARRYING OUT THE INVENTION

Figure 2A:
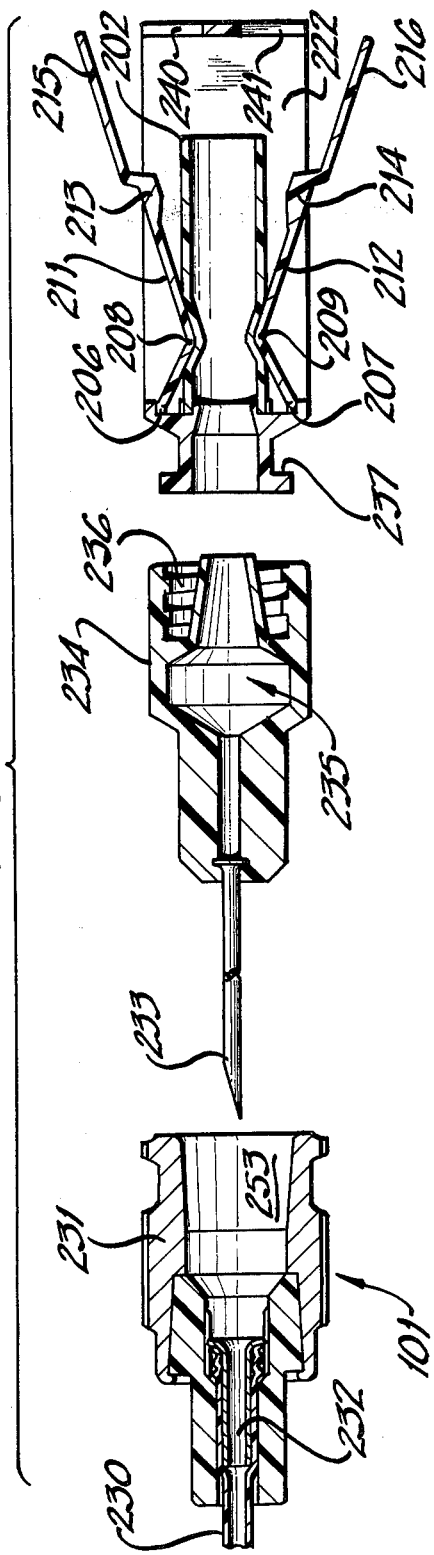
FIGS. 2A, 2B and 2C show various views of a preferred embodiment of the present invention, adapted to be applied to a conventional catheter hub.
Figure 2B:
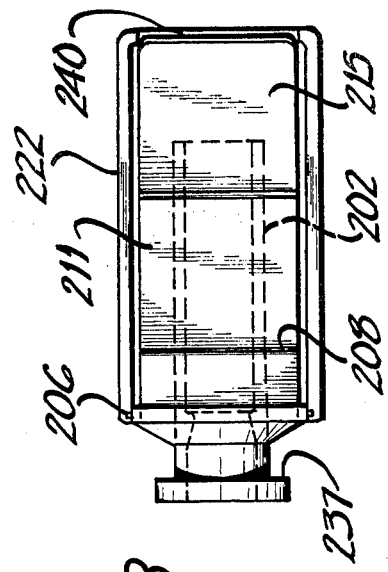

With first reference to FIGS. 1A through 1D inclusive, there is shown in relatively schematic form a sequence of operation in accordance with the principles of the present invention. In FIGS. 1A through 1D, an elastomeric tube or bladder 102 is shown coupled in any suitable fashion to a catheter 101 on one side, and vented on the other side. On the vented side, it is noted that this may be an actual open vent, a porous plug, or an opening into an expanded reservoir for receipt of air to be expelled from the bladder 102 in accordance with the principles of the present invention. Likewise, it is understood that the elastomeric tubular bladder 102 may constitute an integral part of the catheter flashback chamber, or (as is shown in the embodiment of FIGS. 2A and 2B) may be designed as a removable connection for the catheter needle.

In any event, the bladder 102 is embraced by a pair of opposing compression arms 103 and 104. The arms are respectively hinged at points 106 and 107, thereby in essence defining a lever between the respective pivot points 106 and 107, and the opposite extremities, defined by sections 115 and 116 which are adapted to be grasped by the user and pressed together. It will be noted that the compression arms 103 and 104 include, considering from left to right, the hinge points 106 and 107, a first pair of inward pointing angular sections 108 and 109, intermediate essentially straight portions 111 and 112, inwardly raised lands or protuberances 113 and 114, and finally the extremities 115 and 116. In the normal course, the compression arm means 103 and 104 are maintained in the open jaw position generally as shown in FIG. 1A, and in the process of compression, sequentially assume the positions shown in FIGS. 1B through 1D.

It is to be noted that the compression arm means 103 and 104 are of a "semi-rigid" material which, although possessing flexibility, are less deformable than is the elastomeric bladder 102. Hence, the compression arm means 103 and 104 will, upon compression, first serve to deform the bladder 102, but, as is described hereinafter, will thereupon tend to deflect upon application of suitable lever force. Moreover, if the compression arms 103 and 104 are constructed of materials such as polypropylene or semirigid urethane, they may be constructed integrally with a housing for the entire unit, and the hinge points 106 and 107 may simply be constituted as an integral portion thereof adapted to be folded on themselves.

In accordance with the principles of the present invention, the respective opposing point pairs 108 and 109, and 113 and 114, fulfill the dual function, in appropriate sequence, of compressing the bladder 102 in pincer-like fashion, until the respectively opposing points are joined closed, and thereafter constituting a fulcrum for lever action accompanying the subsequent compressive action. Hence, the point pairs 108 and 109, and 113 and 114, are designated "compression fulcra", it being understood that in the course of operation in accordance with the principles of the present invention, the respectively opposing points sometimes act simply for mutual compression, sometimes for both compression and pivot fulcrum action, and sometimes for neither.

Considering FIGS. 1A through 1D as a respective sequence for the same apparatus, wherein like parts are labeled with like reference numerals, there is demonstrated the creation of a partial vacuum, or pulling force on the catheter 101 for purposes of accelerating flashback time. In FIG. 1A, the clamp arms 103 and 104 are shown in a relatively relaxed or open jaw position, that is, with the full length of bladder 102 communicating at equalized pressure with the catheter 101. As the arms 103 and 104 are compressed from the position shown in FIG. 1A to the position shown in FIG. 1B, the first compression fulcrum 108 and 109 presses the elastomeric tube or bladder 102 together, until there is closure at point 117. At this time, the rear or distal portion 118 of the bladder 102 is isolated from the catheter 101, with the pressure in catheter 101 being maintained as it was in the open condition of FIG. 1A. Of course, as the bladder is so compressed, the displaced air is expelled from the distal vented end thereof.

At the time the arms 103 and 104 close the bladder at point 117, and for further compression therebeyond, the points 108 and 109 together act as a fulcrum, and since the arms are spatially fixed at hinge points 106 and 107, such further compression at 115 and 116 causes deflection of the arms 103 and 104 about fulcrum 117, thereby further compressing and evacuating bladder 102 at all points distal to (i.e., to the right of) the fulcrum 117. That is, as the arms are further compressed from the position shown in FIG. 1B, to the position shown in FIG. 1C, the pivot fulcrum of the arms is point 117. As is noted in FIG. 1C, this process continues until the points or surfaces defined by inwardly raised lands or protuberances 113 and 114 compressibly join together. As will be noted from FIG. 1C, the configuration of these lands 113 and 114 in conjunction with the central segments 111 and 112, respectively, of the arms 103 and 104, cause the bladder 102 to be substantially collapsed, and hence evacuated between the point 117 and the point 120 formed by the closed, second compression fulcrum 113 and 114. In FIG. 1C, segment 119 represents the collapsed, evacuated distal segment of the bladder 102.

Further compression of extremities 115 and 116 from the position shown in FIG. 1C, to the position shown in FIG. 1D, causes the point 120, to be the effective pivot fulcrum, and since hinge points 106 and 107 are spatially fixed, such further compression causes the first compression fulcrum points 108 and 109 to separate, likewise opening the closed central segment 119 of the bladder 102 into a proximate chamber 121 which communicates with the catheter 101. Since this occurs with the distal end of the bladder 102 closed at fulcrum point 120, the opening of the bladder at 121 creates a differential negative pressure relative to the pressure of catheter 101, thereby providing a pull on the catheter 101. Of course, if the tip of the catheter is imbedded into tissue, the slight negative pressure will have no substantial effect, but as soon as the needle tip penetrates the vasculature, for example a vein, the negative pressure will serve quickly to pull blood, substantially instantaneously, back into the catheter to equalize the pressure. This substantially instantaneous show of blood in the flashback chamber will indicate to the treating physician or nurse that the catheter is properly positioned in the patient.

Therefore, in sequence, the catheter including or coupled to the apparatus shown in FIGS. 1A through 1D is initially inserted into the flesh of the patient, and the arms are compressed and operate as shown in FIGS. 1A through 1D, as the insertion process is continued. As soon as blood shows in the flashback chamber, the insertion process is completed, and compression force may be released at 115 and 116. Thereupon, in standard fashion, the needle may be removed from the catheter, with the catheter tube remaining indwelling.

Figure 2C:
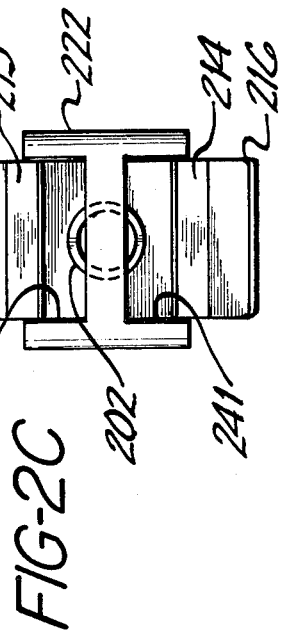

While FIGS. 1A through 1D show a more or less stylized embodiment of the principles of the present invention, FIGS. 2A, 2B and 2C show a somewhat more specific version, adapted to be coupled to a catheter. In particular, FIG. 2A shows a cross-section of a typical catheter, and an embodiment of the principles of the present invention, FIG. 2B shows a top plan view of the apparatus in accordance with the principles of the present invention, and FIG. 2C shows an end view of the same apparatus. In FIG. 2A, the catheter segment 101 is defined by a hub 231, to which a catheter tube 230 is affixed by means of an eyelet 232, which resides within the tube 230 and creates outward pressure for a force fit of the tube 230 in the hub 231. A central chamber 253 is adapted to receive the needle mechanism, including needle hub 234 and the needle itself 233. In operation, the needle hub 234 resides in the cavity 253 of the catheter hub 231, with the needle 233 extending through the catheter tube 230 and penetrating slightly outwardly therefrom. Within the needle hub 234 is a chamber 235, advantageously useful as a flashback chamber, provided the hub 234 includes at least a portion which is transparent or transluscent to show presence of blood in the cavity 235.

The FIG. 2A drawing shows the differential flashback accelerator embodying the principles of the present invention being distinct from and connectable to the needle hub 234 by means of a luer connection 236 and 237. Quite clearly, depending upon the desire of the designer, these two parts could easily be fabricated as a single part, thereby disposing of the need for the luer connection 236 and 237.

As will be noted from FIGS. 2A, 2B and 2C, essentially embodying the principles of the present invention, the tubular elastomeric bladder 202 is coupled, as desired, to the proximate end of the evacuating unit, and a protective surrounding wall 222 is open at top and bottom to permit compression and flexure of the respectively opposing arms. Each arm has, like the symbolically shown counterpart from FIGS. 1A through 1D, a hinged portion 206 and 207, a first pair of opposing compression fulcrum points 208 and 209, a second such pair of compression fulcrum points 213 and 214, intermediate sections 211 and 212 separating the respective compression fulcra, and at the extremities handles 215 and 216 adapted for compression thereof. Optionally, a pair of notches 240 and 241 accommodate the handles 215 and 216 at the extremities of compression. As shown in FIGS. 2A, 2B and 2C, the bladder 202 is unvented, but extends a distance beyond the second compression fulcrum in order to accommodate the differential pressure therefrom. It is understood that the tube may but need not be vented. Operation of the embodiment of FIGS. 2A, 2B and 2C is as shown symbolically in FIGS. 1A through 1D and previously described in conjunction therewith.

It is understood that the foregoing sets forth preferred and illustrative embodiments of the principles of the present invention, but that numerous alternative embodiments could likewise be employed without departure from the spirit or scope of the present invention. For example, the embodiments described herein relate to a pair of pivotable, mutually opposing compression arms defining the respective compression fulcra. It is within the contemplation of the principles of the present invention that the same effect could be achieved by having a fixed, rather than pivotable arm (a "floor") on one side, with just the other side (e.g., the top) being pivotable downwardly toward the floor, nevertheless performing the same compression/evacuation/proximal reopening functions as set forth in accordance with the embodiments shown herein. Likewise, as stated, embodiments of the principles of the present invention may be directly incorporated into the cannula portion of the catheter assembly, may be discrete and connectable therewith, as shown, or for that matter may be connectable into another portion of the assembly (e.g., directly into the catheter 101 through an ancillary coupling, not shown). Further, the selection of materials useful in accordance with the principles of the present invention provides extensive freedom to the designer. The elastomeric bladder material 202 may be freely chosen, as may the materials for the compression arms, so long as the bladder is more deformable than are the arms themselves. The particular shape of the arms is less critical than is their function, of first sealing the bladder at the first fulcrum, then evacuating the bladder distally, then sealing it at the second fulcrum and reopening the first fulcrum to create a negative pressure at the proximal end.

It is likewise to be noted that although the principles of the present invention, and embodiments thereof, are set only in terms of the vascular flashback function, they will no doubt enjoy substantial equivalent application to a variety of otherwise conventional fluid aspiration applications.

I claim:

1. In a vascular fluid withdrawal or introduction device the improvement comprising, apparatus for confirming placement through creation of flashback, including:
   an elastomeric housing defining a chamber, adapted to communicate with said device at one end; and
   at least a pair of oppositely facing compression arm means embracing said housing, said means being hingedly coupled at said one end, said arm means having at least two compression fulcra intermediate its ends,
   whereby compression together of said arms causes said fulcra successively to compress said chamber closed from said one end to the other, preceding fulcra being disengaged as successive fulcra are engaged.

2. Apparatus as described in claim 1 wherein said compression arm means define two said fulcra, each fulcrum being defined by a pair of respectively opposing sections, engageable with one another compressively to close said housing therebetween.

3. Apparatus as descibed in claim 2 wherein at least one of said compression arm means is flexibly deformable but less so than is said housing.

4. Apparatus as described in claim 3 wherein the respective relevant positions of said arm means are:
   (a) fully open, housing undeformed;

(b) partially compressed, said arm means pivoting at said one end, said first fulcra deforming said housing to form compressive chamber closure;

(c) further compression, said first fulcrum closed and acting as pivot point, and said second fulcrum closing together to form compressive chamber closure; and (d) still further compression, said second fulcrum closed and acting as pivot point, and opening said first fulcrum, thereby to reopen said housing at a negative differential pressure relative to said device.

5. Apparatus as described in claim 3 wherein both said compression arm means are flexibly deformable, and wherein said first and second fulcra are each defined by respectively opposing prominent points separated by a segment adapted to maintain said chamber completely collapsed between said fulcra when both said fulcra are closed.

* * * * *